US008665440B1

(12) United States Patent
Kompaniets et al.

(10) Patent No.: US 8,665,440 B1
(45) Date of Patent: Mar. 4, 2014

(54) PSEUDO-APPOSITION EYE SPECTRAL IMAGING SYSTEM

(75) Inventors: Iouri V. Kompaniets, Long Beach, CA (US); Tomasz Jannson, Torrance, CA (US); Ranjit Pradhan, Torrance, CA (US)

(73) Assignee: Physical Optics Corporation, Torrance, CA (US)

( * ) Notice: Subject to any disclaimer, the term of this patent is extended or adjusted under 35 U.S.C. 154(b) by 305 days.

(21) Appl. No.: 13/025,096

(22) Filed: Feb. 10, 2011

(51) Int. Cl.
*G01J 3/46* (2006.01)
*G01N 21/25* (2006.01)

(52) U.S. Cl.
USPC ........... 356/419; 356/402; 356/425; 356/416; 356/403

(58) Field of Classification Search
USPC .................................................. 356/402–425
See application file for complete search history.

(56) References Cited

U.S. PATENT DOCUMENTS

| 6,236,474 | B1 * | 5/2001 | Mestha et al. | 358/520 |
| 7,587,109 | B1 * | 9/2009 | Reininger | 385/116 |
| 2006/0023218 | A1 * | 2/2006 | Jung et al. | 356/419 |
| 2007/0025512 | A1 * | 2/2007 | Gertsenshteyn et al. | 378/86 |
| 2009/0290236 | A1 * | 11/2009 | Wang et al. | 359/723 |

* cited by examiner

*Primary Examiner* — Tarifur Chowdhury
*Assistant Examiner* — Sunghee Y Gray
(74) *Attorney, Agent, or Firm* — Sheppard Mullin Richter & Hampton LLP

(57) ABSTRACT

A spectral imaging system comprises a plurality of spectral units arranged in an array, each spectral unit of the plurality of spectral units comprising: a microlens having an optical axis; a spectral filter having a center wavelength and aligned with the optical axis; a fiber optic bundle, the fiber optic bundle having a curved light receiving surface and a planar light output surface, wherein the curved light receiving surface is aligned with the optical axis; and a plurality of pixel sensors configured to receive light from the planar light output surface of the fiber optic taper portion.

42 Claims, 13 Drawing Sheets

PSEUDO-APPOSITION EYE SPECTRAL IMAGING SYSTEM

TECHNICAL FIELD

The present invention relates generally to imaging systems, and more particularly, some embodiments relate to spectral imaging systems.

DESCRIPTION OF THE RELATED ART

Currently available spectral imaging systems typically use methods such as color wheels, prisms, and liquid-crystal tunable filters. These systems are inadequate for miniaturized camera systems because of their size, weight, and cost. Commercial multispectral camera systems frequently use tunable filters and monochrome sensors with various lens options (15 to 100 mm focal length) that make their physical size prohibitive for military, medical, or machine vision applications. In addition to making these systems bulky and expensive, these difficulties have prevented development of handheld versions.

BRIEF SUMMARY OF EMBODIMENTS OF THE INVENTION

According to various embodiments of the invention, a multi-spectral imaging system is presented. The system comprises an array of parallel spectral channels, each channel is an independent imaging system, with a microlens and a spectral filter. Imaging multiplicity arising from the array of microlenses is used to provide a plurality of spectrally filtered images. In some embodiments, the spectral filters are narrowband interference filters that exhibit the Bragg effect of blue-shifted wavelength filtering for increasing angle of incidence. This allows the system to provide hyperspectral imaging capabilities through the use of virtual channels.

According to an embodiment of the invention, a spectral imaging system comprises a plurality of spectral units arranged in an array, each spectral unit of the plurality of spectral units comprising: a microlens having an optical axis; a spectral filter having a center wavelength and aligned with the optical axis; a fiber optic bundle, the fiber optic bundle having a curved light receiving surface and a planar light output surface, wherein the curved light receiving surface is aligned with the optical axis; and a plurality of pixel sensors configured to receive light from the planar light output surface of the fiber optic taper portion.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Filter 7 illustrates a graph of a spectro-angular map implemented in accordance with an embodiment of the invention.

Figure 8:
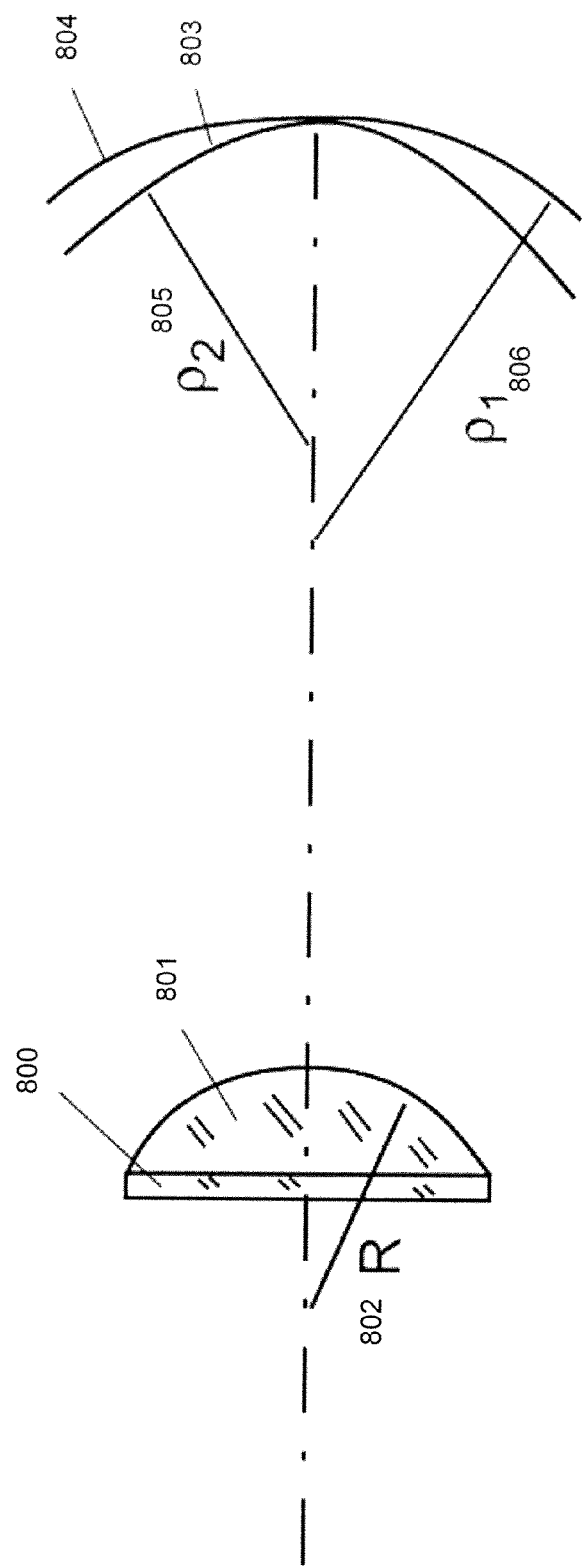

FIG. 8 illustrates a comparison between the geometric loci of focal points of a filter and lens combination and a lens alone.

Figure 9:
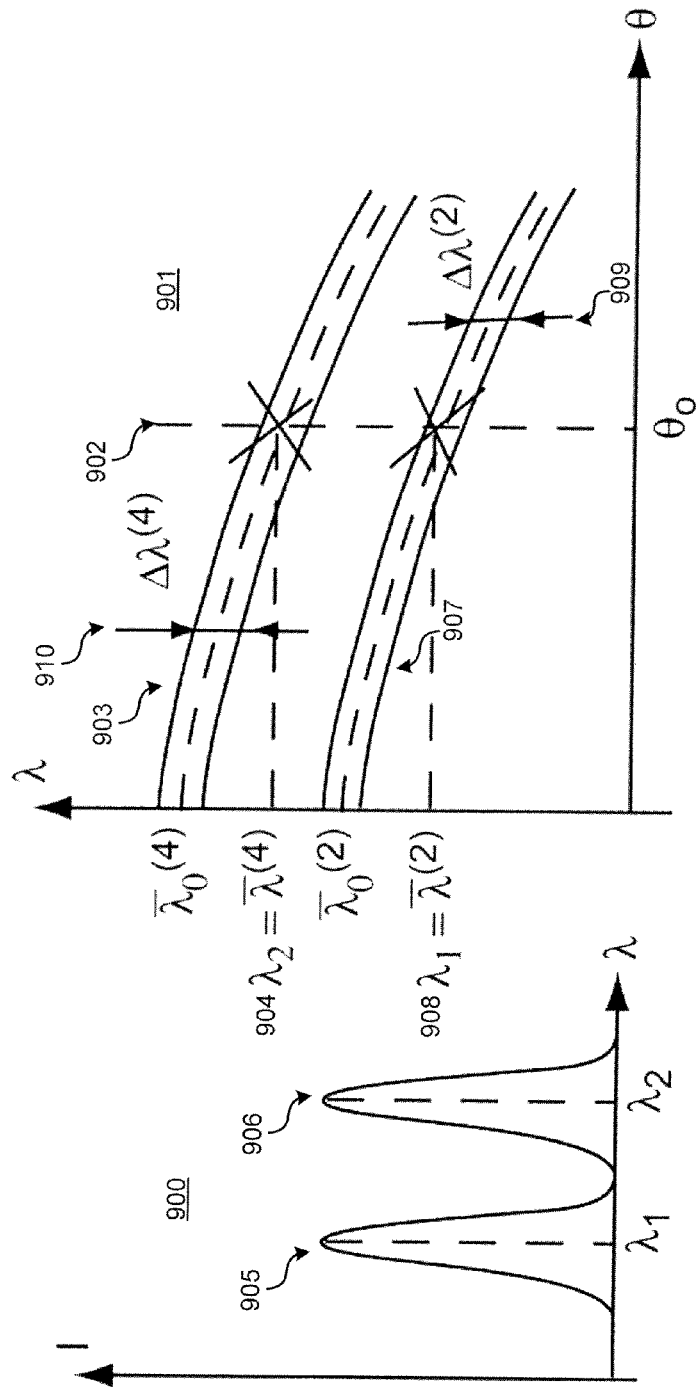

FIG. 9 illustrates a spectral signature identification process in a hyperspectral imaging system implemented in accordance with an embodiment of the invention.

Figure 10:
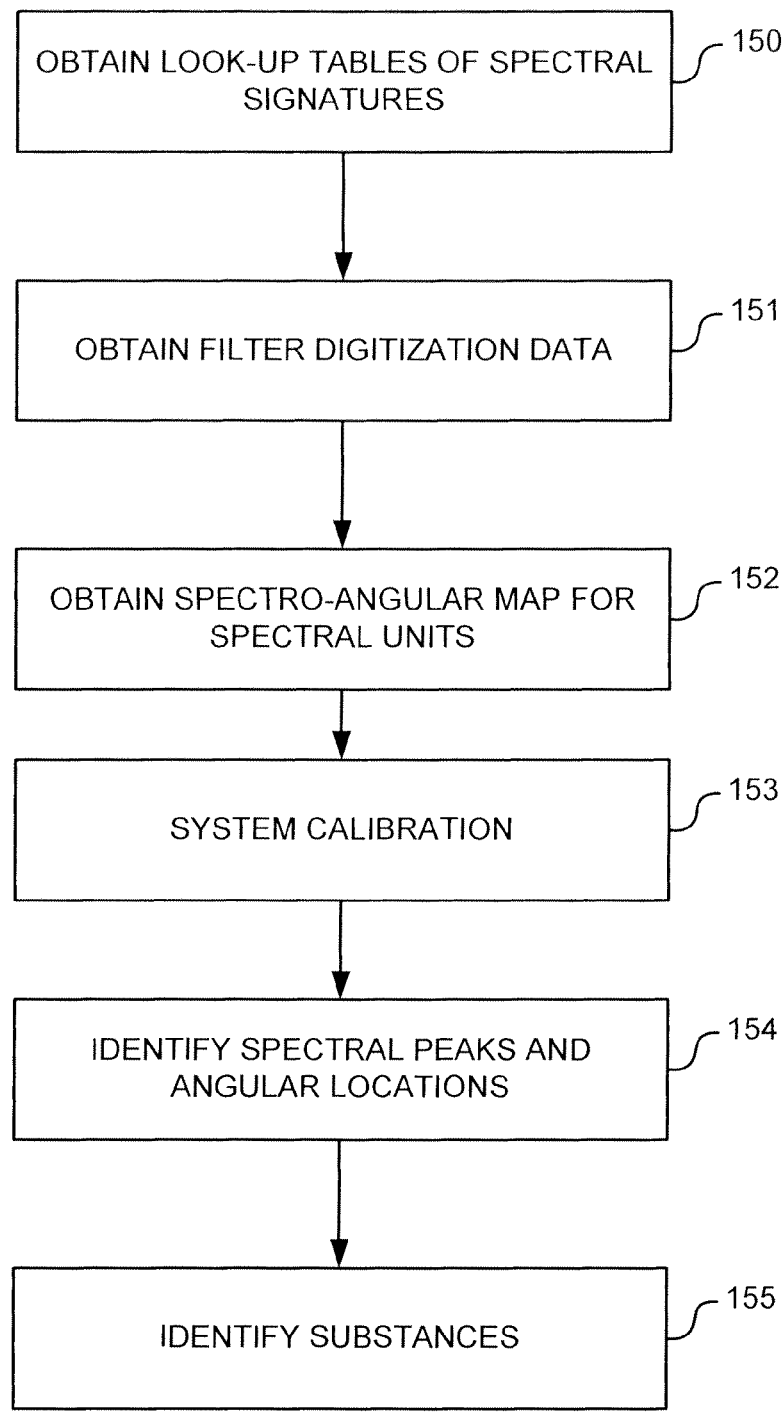

FIG. 10 illustrates a method of system operation implemented in accordance with an embodiment of the invention.

Figure 11:
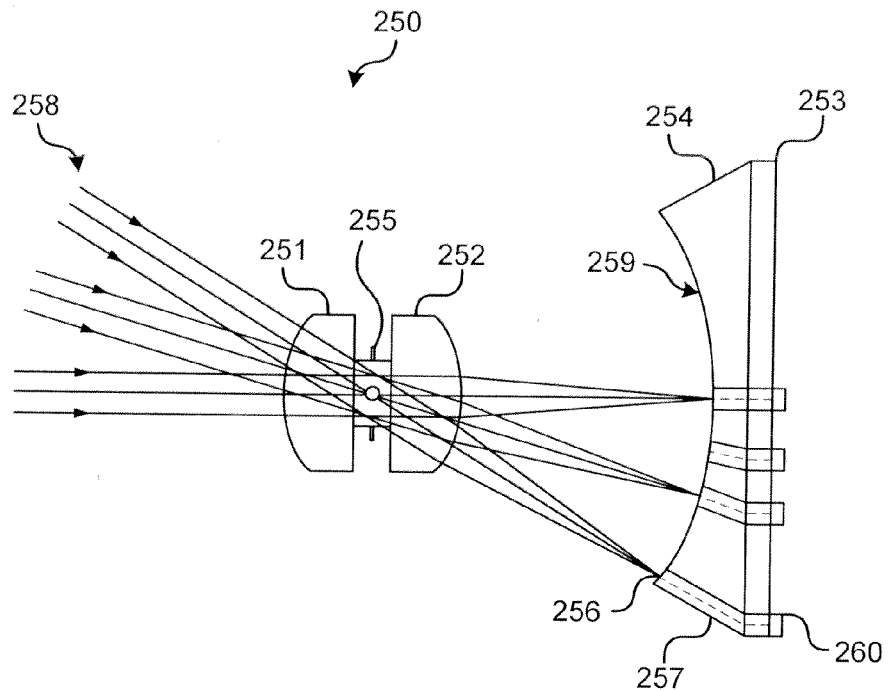

FIG. 11 illustrates a spectral unit a further embodiment of the invention.

Figure 12:
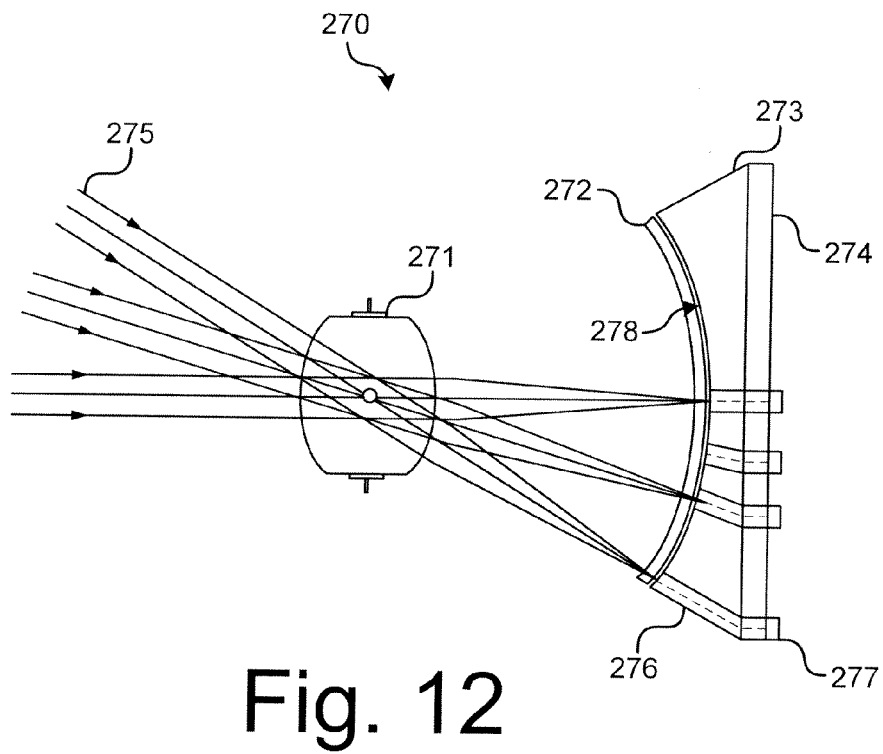

FIG. 12 illustrates a spectral unit of another embodiment of the invention.

Figure 13:
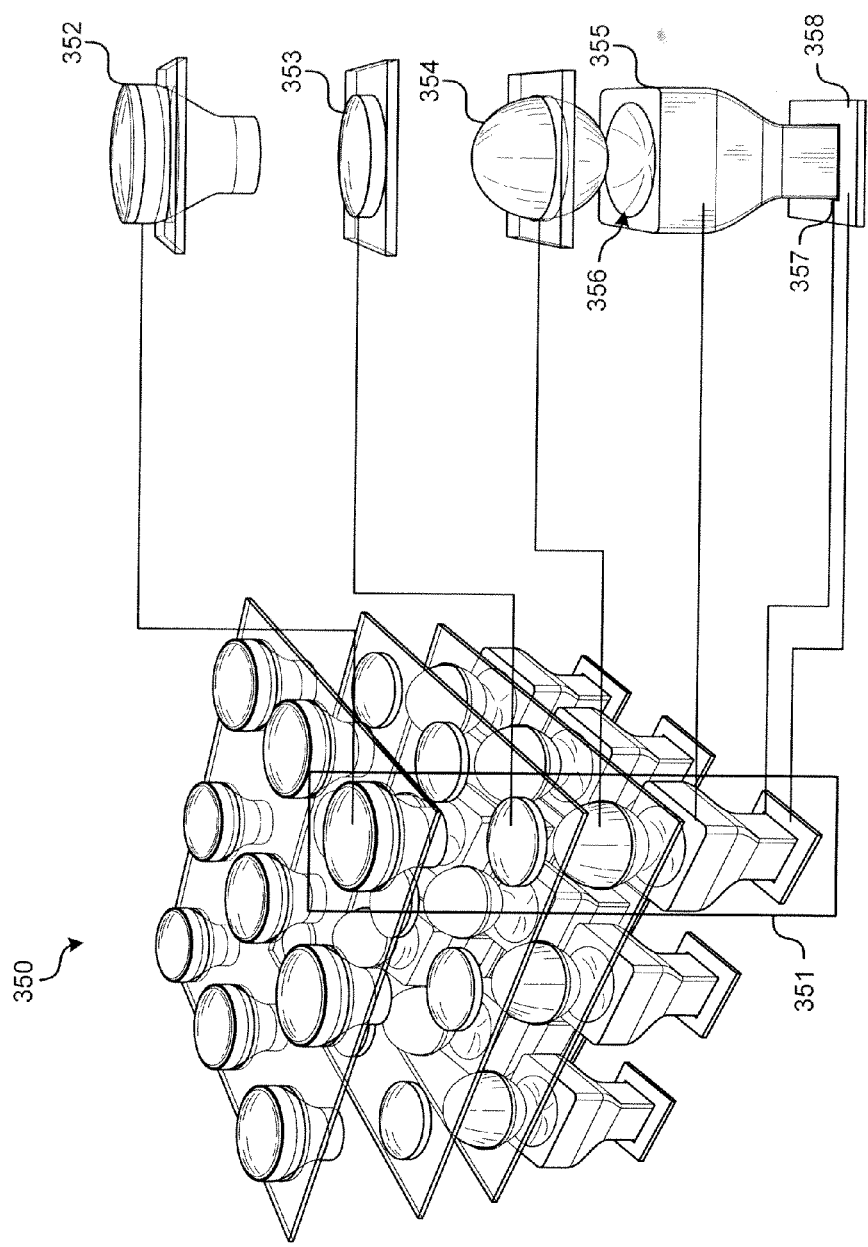

FIG. 13 illustrates an embodiment of the invention employing a telescope array.

Figure 14:
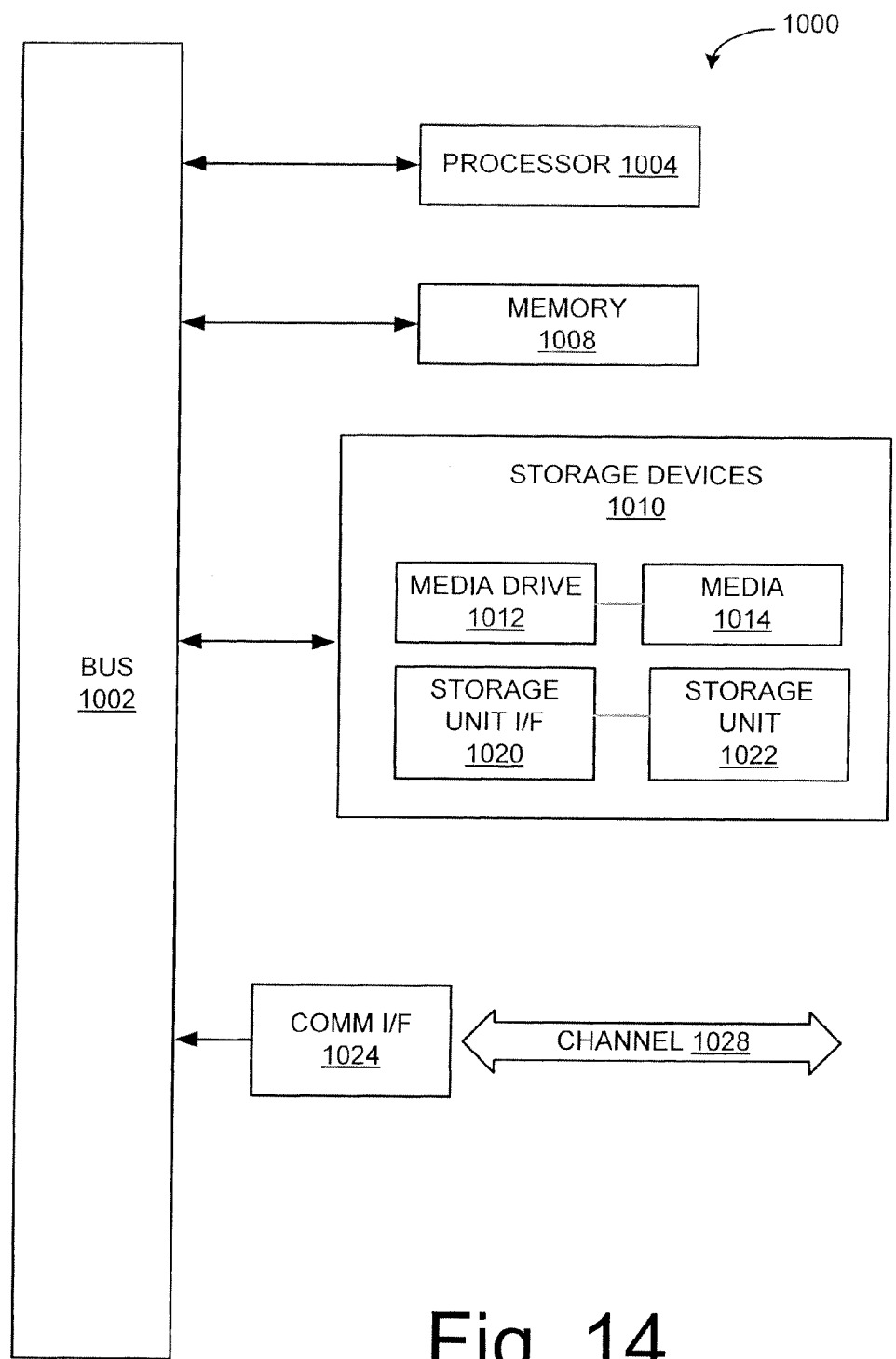

FIG. 14 illustrates an example computing module that may be used in implementing various features of embodiments of the invention.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

The present invention is directed toward a system and method for multispectral imaging. In one embodiment, the system comprises a plurality of spectral units, the spectral units comprising optical trains having microlenses, spectral filters, and a photodetector.

Figure 1:
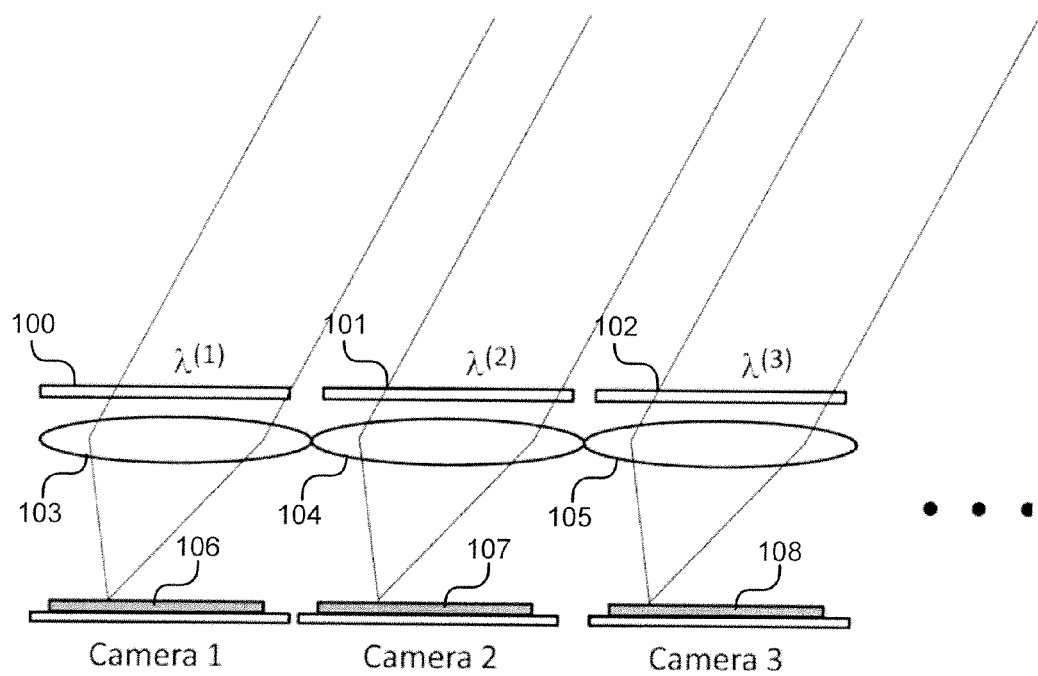
FIG. 1 illustrates a first embodiment of the invention.

FIG. 1 illustrates a first embodiment of the invention. In this embodiment a plurality of lenses 103, 104, and 105 image a common field of view. Each lens is provided a corresponding spectral filter 100, 101, and 102, respectively. In the illustrated embodiment, the spectral filters 100, 101, and 102 comprise narrow band interference filters and are positioned in front of their respective lenses to preserve the planar nature of the wavefront of light arriving at the system. In other embodiments, other filters or types of filters can be used and alternative positions or orientations for the filters may be employed. In this example, each interference filter 100, 101, 102, has a different center Bragg wavelength, $\lambda^{(1)}$, $\lambda^{(2)}$, $\lambda^{(3)}$, respectively, representing different spectral bands for each lens.

Each lens 103, 104, and 105, further has its own camera or other photodetection system 106, 107, and 108, respectively. Preferably, cameras 106, 107, and 108 employ two-dimensional photoreception at the focal plane of the lens. In some embodiments, these cameras 106, 107, and 108 may comprise image sensors, such as pixel sensors and CCDs; fiber optic ends; or other photoreceiver or photodetector elements.

Figure 2:
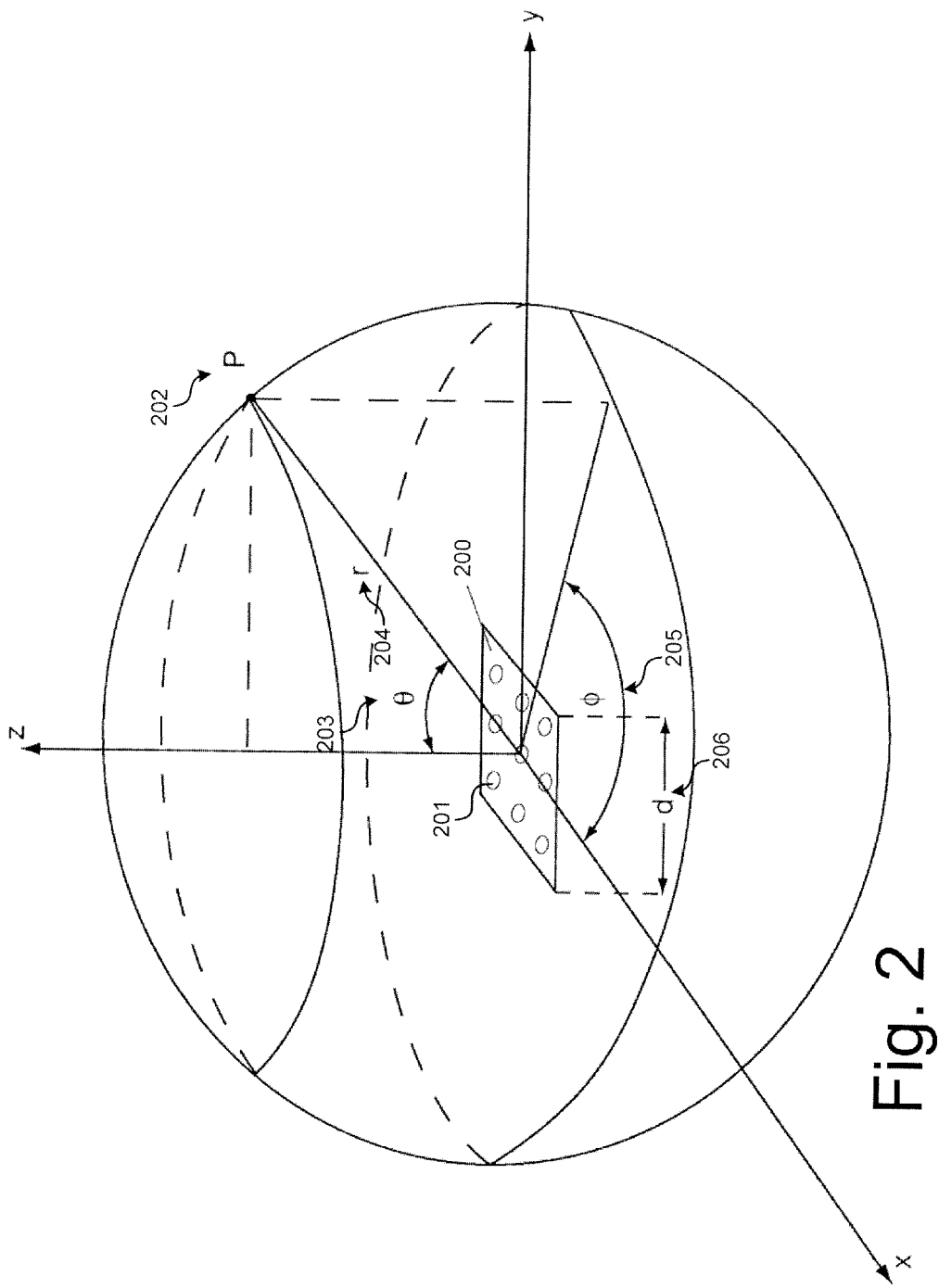
FIG. 2 illustrates variables and system parameters for assistance in describing various aspects of embodiments of the invention.

FIG. 2 illustrates variables and system parameters for assistance in describing various aspects of embodiments of the invention. The illustrated geometry is used herein to describe various aspects of the invention. A world point P 202 is located at a distance r 204 from the imaging system 200. The angle of incidence θ 203 of rays from P 202 to the system 200 is measured with respect to the optical axis of the system z. The azimuthal angle φ 205 is measured according an arbitrary axis perpendicular to the optical axis, x. The system has a characteristic size d 206 that is a measure of the largest dimensions of the systems. For example, d may be approximately the maximal distance between spectral units 201 along a side of the imaging system array 200. In typical system implementations, r>>d, so the entire system 200 may be treated as located at a single point. (In other words, the specific location of a particular spectral unit 201 in the system 200 does not impact that particular spectral unit's spectral image.) Under this approximation, each world object point P 202 within the system's 200 field of view may be represented by a plane wave with direction in spherical coordinates (θ, φ).

Referring again to FIG. 1, each spectral band of the Filters 100, 101, 102, etc. ... may be represented at normal incidence ((θ=0), i.e., parallel to the optical axis), by its central Bragg wavelength $\bar{\lambda}^{(i)}$, where i indexes the spectral units of the imaging system. In embodiments employing narrowband interference filters, this wavelength is shifted into shorter wavelengths for slanted angles of incidence (θ>0; θ≤π/2) due to the Bragg effect. This Bragg effect results in a blue-shift for increasing angle of incidence. In embodiments where the system is monitoring only plane waves (for example, where the assumption d>>r holds), the lenses 103, 104, 105, are only required to produce a plane wave to image point transformation, equivalent to a Fourier transform. The geometrical loci of these image points will be similar to Petzval's surface, but with a reduced radius of curvature resulting from the blue shifting Bragg effect of the filters 100, 101, and 102. In particular embodiments, the microlenses 103, 104, and 105, used in the system may comprise ball lenses.

Figure 3:
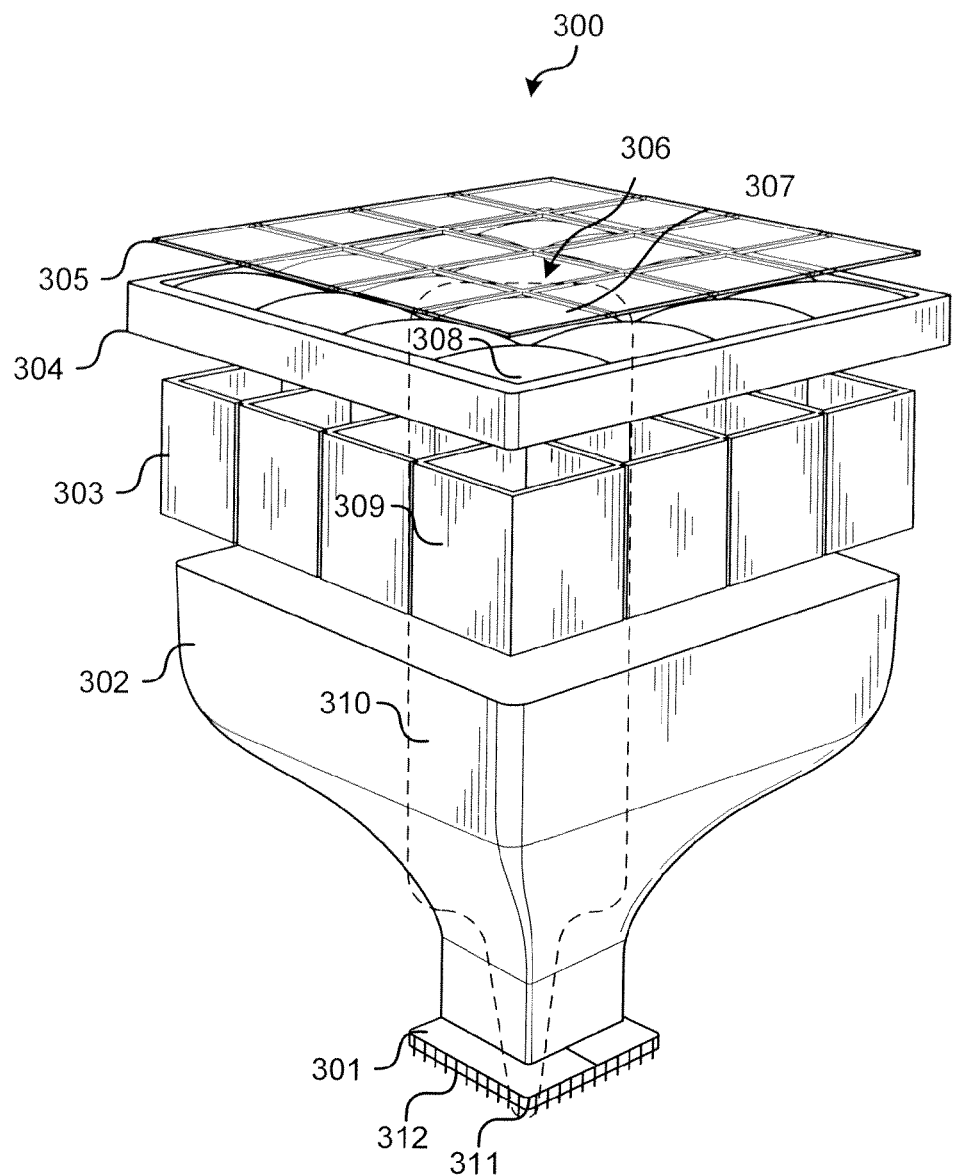
FIG. 3 illustrates a second embodiment of the invention, illustrated in an exploded view.

FIG. 3 illustrates a second embodiment of the invention, illustrated in an exploded view. The illustrated multispectral imaging system 300 comprises an array of spectral filters 305. The spectral filters 305 comprise pass-band spectral image filters that pass light within a spectral band centered around a particular center frequency. The illustrated spectral filters 305 are configured to have varying center wavelengths to provide a number of differently filtered images of the same scene (or roughly the same scene, depending on parallax effects or view angles). This allows the imaging of a scene across a predetermined band at varying wavelengths. In particular embodiments, the filters 305 may comprise narrowband interference filters with full widths at half maximum (FWHM) of about 4-5 nm, although other values can be used. Typical spectral transparency at the center wavelength of filters 305 is about 90%. As described herein, these filters may display Bragg effect blue-shifting for varying angles of incidence, allowing increased spectral sensitivity through the implementation of virtual spectral channels.

Disposed below the array of spectral filters 305 is a corresponding array of microlenses 304. The microlenses 304 receive the filtered image signals from the filters 305 and focus them onto a desired plane. As shown, in the illustrated example, each microlens 304 is positioned immediately below its corresponding spectral filter 305. In typical embodiments, the received image signals are approximately plane waves received from distant world points. The microlenses 304 therefore perform a plane wave to single point transformation. In some embodiments, these microlenses 304 may comprise simple spherical lenses, such as ball lenses.

Coupled to the array of microlenses 304 is a corresponding microchannel array 303. The microchannel array 303 is configured to separate the image signals from the lenses of the microlens array 304 and prevent crosstalk between the physical channels. In the illustrated embodiment, microchannel array 303 is positioned so that each microchannel in the array 303 is aligned with its corresponding microlens 304.

A fiber optic taper 302 is coupled the microchannel array 303 and an image sensor 301. The fiber optic taper 302 receives the image signals from the array of microlenses 304 at a light receiving side, demagnifies the ensemble, and provides the image signals to the image sensor 301. In other embodiments, the fiber optic taper 302 may be optionally omitted. In such embodiments, the microchannel array 303 may be coupled directly to the sensor 301. In such embodiments, sensor 301 is preferably sized such that it has an effective sensor area at least as large as the microchannel array 303.

In other embodiments, the microchannel array 303 may be optionally omitted. In such embodiments, the fiber optic taper 302 may be adapted to provide the functionality of the microchannel array 303 or crosstalk may be avoided using other structures or techniques. For example, gradient index optics (GRIN) lenses and spectral filters may be disposed directly in the ends of the optical fibers of the fiber optic taper.

In some embodiments, the image sensor 301 may comprise an sCMOS sensor array sensitive from (200-1,000 nm), and in further embodiments may include SWIR (1,000-1,700 nm) or MWIR+LWIR (3-14 micron) sensor arrays. A processing module 312, such as an FPGA or DSP image processor, may be coupled to the image sensor 301. In the illustrated embodiment 300, the arrays of filters 305, microlenses 304, and microchannels 303 are planar arrays, such as N×M grids (a 4×4 grid is shown). In other embodiments, the arrays may be spherical, semispherical, linear, or in some other configuration, and various numbers of elements may make up the arrays. In particular embodiments, the lens array 304 may comprise a microlens array with pitch ranges from 100 to 1,000 microns, focal lengths between 0.5 and 5 mm, and lens diameters from 150 to 1,000 μm.

The illustrated arrays 305, 304, and 303 provide the system 300 with a plurality of physical channels or spectral units 306. Each spectral unit 306 in the illustrated example comprises a filter 307, a lens 308, an image separation channel 309, a bundle of optical fibers 310, and a number of pixel sensors 311 of the image sensor 301. The filter 307, lens 308, channel 309, and the light receiving side of the bundle 310 are preferably aligned with respect to a common optical axis. As would be apparent to one of ordinary skill in the art after reading this description, other structures or techniques can be used to provide a system with a plurality of physical channels or spectral units.

Figure 4:
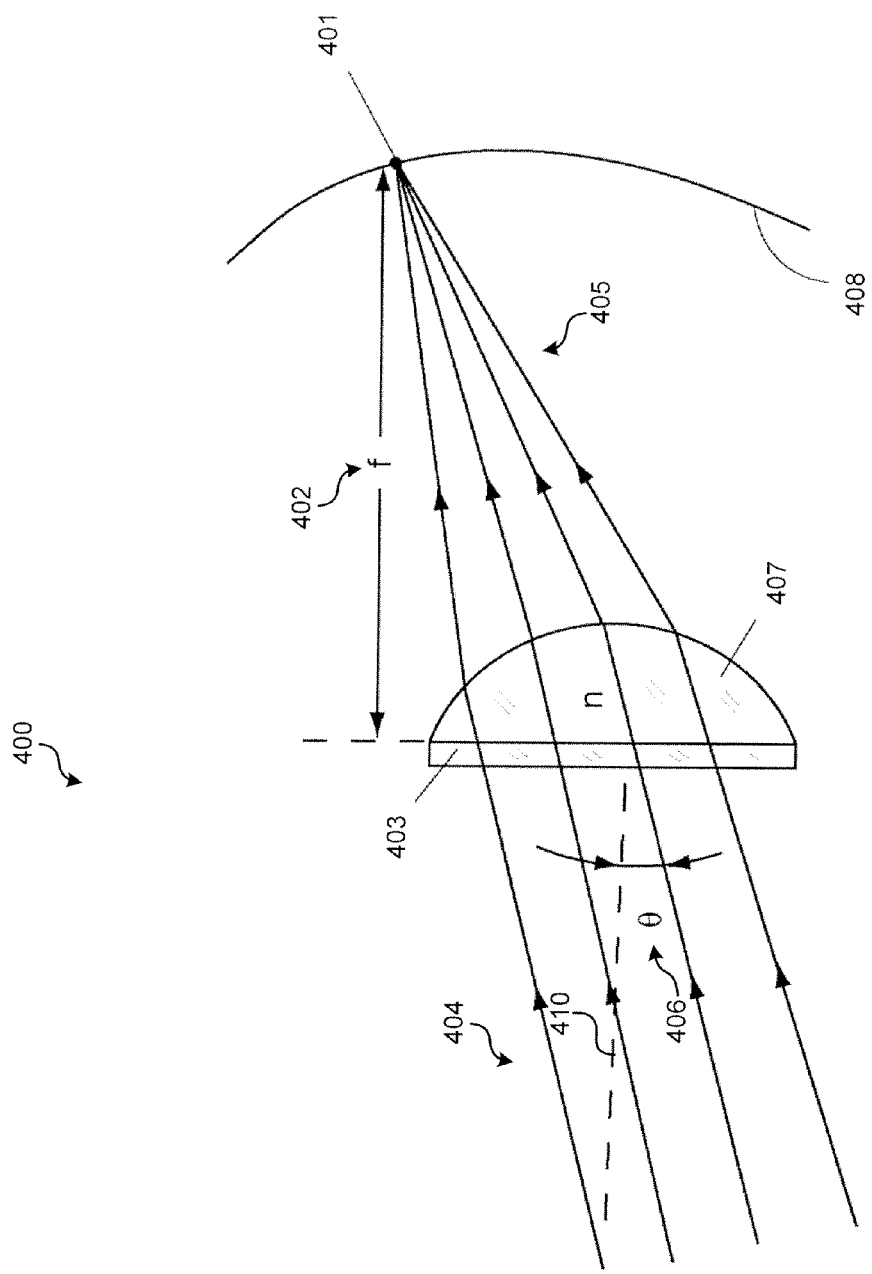
FIG. 4 illustrates a spectral unit implemented in accordance with an embodiment of the invention.

FIG. 4 illustrates a spectral unit implemented in accordance with an embodiment of the invention. In the illustrated example embodiment, the spectral unit 400 comprises a lens 407 with index of refraction n and focal length f. In the illustrated embodiment, the lens 407 comprises a plano-convex lens. However, other converging lenses may be employed in other embodiments. A spectral filter 403, such as, for example, an interference filter, is disposed on the planar side of the lens 407. A beam of light 404 impinges upon the spectral unit 400 with an angle of incidence θ 406, with respect to the optical axis 410. When the beam of light 404 is a plane wave, it is focused to a point 401. The perpendicular distance 402 of the point 401 varies according to the angle of incidence θ 406, forming a curved surface. In the illustrated embodiment, a light receiving surface 408 is disposed to coincide with the curved surface of geometric foci of plane waves 404 transformed by the spectral unit's 400 filter 403 and lens 407.

In the illustrated embodiment, the filter 403 comprises an interference filter that exhibits a blue-shift Bragg effect. Without the presence of an interference filter 403, the geometric loci of foci points for plane waves of varying angle of incidence would describe what is known in the art as a Petzval's surface. However, in typical lenses, the index of refraction n varies according the wavelength of the refracted light beam 404. As the angle of incidence θ 406 increases, the center wavelength of the filter 403 is decreased. The blue shift is described by the following equation:

$$\lambda = \lambda_0 \sqrt{1 - \frac{\sin^2\theta}{n^2}} \quad (1)$$

where $\lambda_0$ and $\lambda$ are equivalent wavelengths under normal and slanted incidence, respectively, θ is the incidence angle in air, and n is the refractive index of lens (and filter, in the ideal case). Accordingly, as the angle of incidence 406 increases, the wavelength of the plane waves emitted by the filter 403 is blue-shifted. This change in wavelength results in the plane waves being exposed to a varying index of refraction n. This modifies the curvature of the surface 408, as discussed further below.

Snell's law is (where θ' is incidence angle in median):

$$\sin\theta = n\sin\theta' \quad (2)$$

and, after the paraxial approximation:

$$\theta = n\theta', \text{ for } \theta \ll 1 \quad (3)$$

and, $$\lambda = \lambda_0 \left(1 - \frac{\theta^2}{2n^2}\right) \quad (4)$$

which has a parabolic dependence, with $$\theta = \frac{\pi}{180}\theta° \quad (5)$$

converting between angle in radians and angle in degrees. In Table 1, Eq. (1) is illustrated for n=1.55, including the case with the paraxial approximation (for $(\lambda/\lambda_0)_p$), and the exact case (for $(\lambda/\lambda_0)$).

TABLE 1

| Eq. (1) for n = 1.55, Including Paraxial Approximation $(\lambda/\lambda_0)p$, and Exact Formula $(\lambda/\lambda_0)$ | | | | | | | | |
|---|---|---|---|---|---|---|---|---|
| θ | 0° | 10° | 20° | 30° | 40° | 50° | 60° | 70° |
| $(\lambda/\lambda_0)_p$ | 1 | 0.99 | 0.97 | 0.94 | 0.90 | 0.84 | 0.77 | 0.69 |
| $(\lambda/\lambda_0)$ | 1 | 0.99 | 0.97 | 0.95 | 0.91 | 0.87 | 0.83 | 0.78 |

Figure 5:
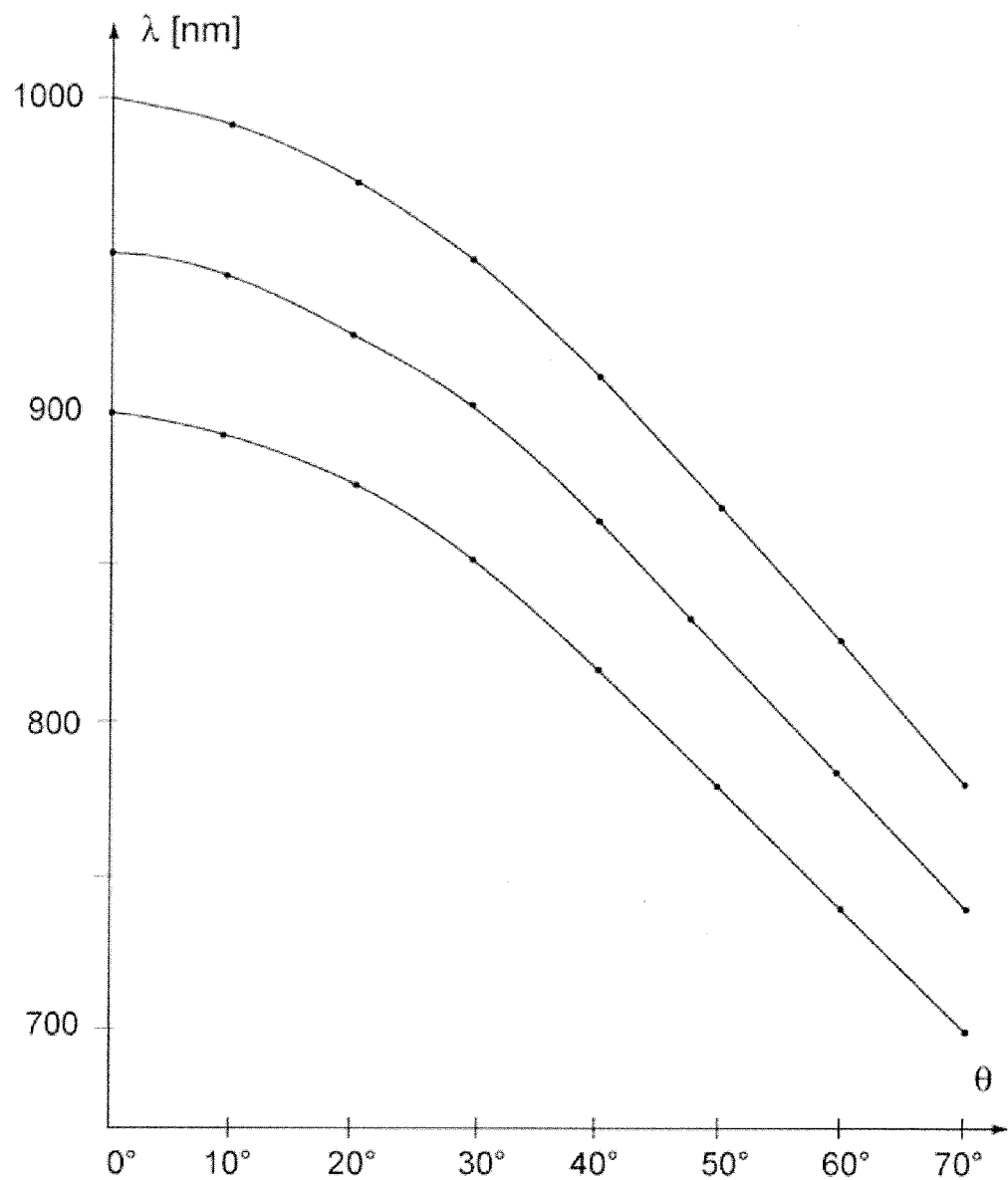
FIG. 5 graphs the wavelength/angular dependence for incident light of three wavelengths and for a lens with refractive index n=1.55.

FIG. 5 illustrates the result of formula (1) for three wavelengths and for n=1.55. As the graph illustrates, there is significant wavelength shift into shorter wavelengths. For larger incidence angles (θ=70°) the shift is about 200 nm.

Figure 6:
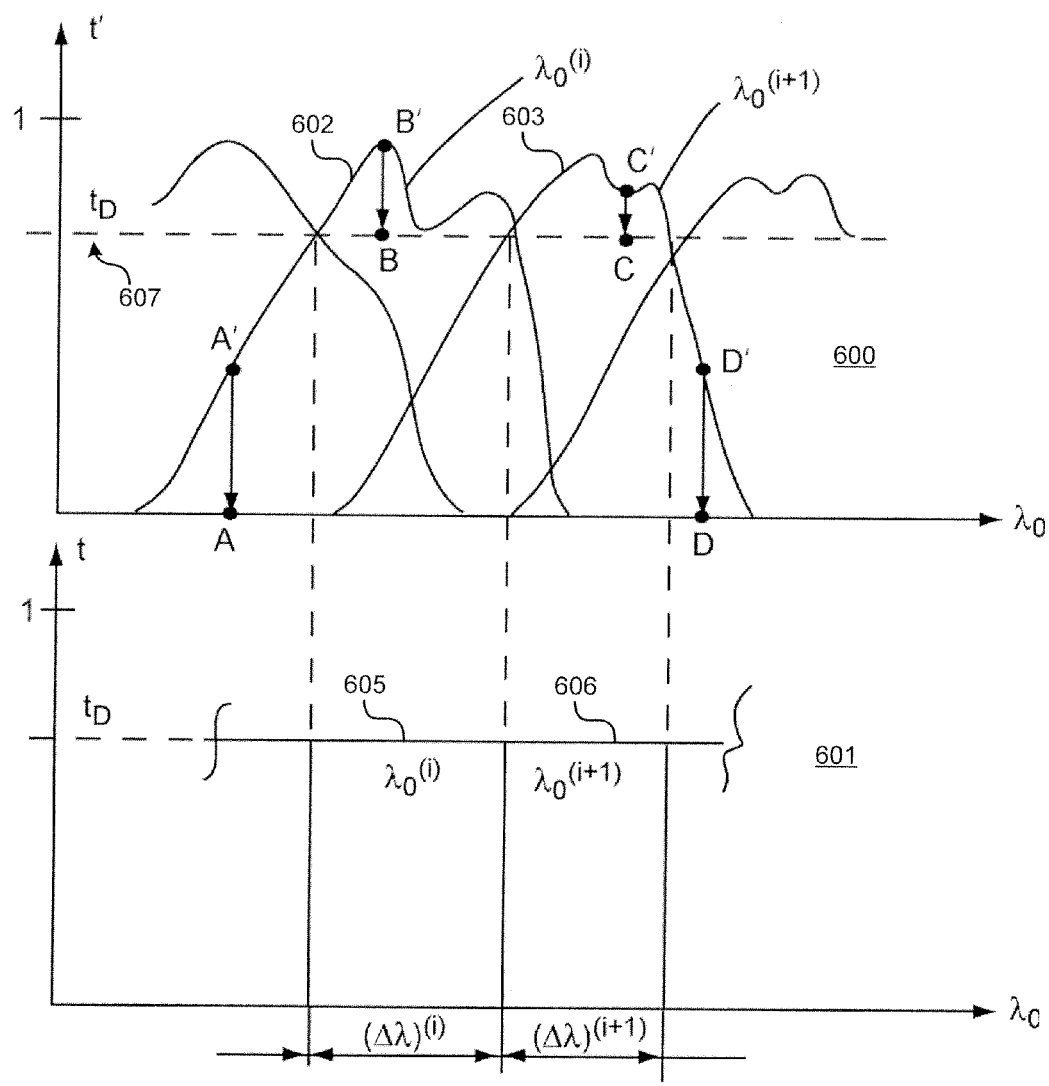
FIG. 6 illustrates a filter binarization process implemented in accordance with an embodiment of the invention.

As described above, in some embodiments of the invention, a computer system comprising hardware or software logic is coupled to the image sensor to process the signal received from the image sensor. One such processing operation is a digitization procedure where the signal from a particular filter is digitized to normalize the filter's transmissivity in the digital domain. FIG. 6 illustrates an example of one such procedure where the signal from pluralities pixels corresponding to different filters is clipped to effectively normalize the different filters' responses. In the illustrated process, the upper graph 600 illustrates a plurality of transmissivity profiles 602, 603 for different filters as received from the image sensor. The lower graph 601 illustrates the axes are wavelength and the vertical axes are transmissivity. Each curve of graph 600, such as curves 602 and 603, illustrates the transmissivity of a particular filter for light impinging thereon with a 0° angle of incidence. For example, curve 602 illustrates the transmissivity of the ith filter, and curve 630 illustrates the transmissivity of the i+1th filter.

The illustrated process binarizes the filter systems spectral characteristics. The real filter spectral characteristics are normalized in the electronic domain into a binarized regular form. In the illustrated embodiment, each spectral point's transmissivity is normalized; i.e. its value is multiplied by some factor, depending on threshold value, $t_D$, 607, in the following form (i.e., the spectral points are clipped):

$$\text{if } t \geq t_D, \text{ then } t = t_D \quad (6)(a)$$

$$\text{if } t < t_D, \text{ then } t = 0 \quad (6)(b)$$

For example, for point A', $t < t_D$, so the new point A is moved to zero, while for point B', $t > t_D$, so the new (normalized) point B' moves to the clipped $t = t_D$. The result is shown in graph 302, where two filter exemplary spectral characteristics: $\lambda_0^{(i)}$ 605, $\lambda_0^{(i+1)}$ 606, for the ith and (i+1)th filters, have been normalized to clipped shapes with widths: $\Delta\lambda^{(i)}$ and $\Delta\lambda^{(i+1)}$, respectively.

According to Eq. (1), the relation between wavelengths at normal incidence (θ=0), and slanted incidence (θ>0) has the form:

$$\lambda = \lambda_0 a \quad (7)$$

where the factor, a, depends on the angle of incidence θ but does not depend on λ, and where λ and $\lambda_0$ are the wavelengths for slanted and normal incidences, respectively. Therefore, for an arbitrary blue-shifting filter, indexed by i:

$$\lambda^{(i)} = \lambda_0^{(i)} a \quad (8)$$

and the spectral distance between $\lambda^{(i)} = \lambda_0^{(i)}$, is $$\lambda_0^{(i)} - \lambda^{(i)} = \lambda_0^{(i)}(1-a) \quad (9)$$

i.e., it is proportional to factor: (1-a), which, for equal θ values is the same for different values of λ. Therefore, as the value of $\lambda_0$ increases, the distance increases:

$$\lambda_0^{(i)} \nearrow \Rightarrow [\lambda_0^{(i)} - \lambda^{(i)}] \nearrow \quad (10)$$

Also, from Eq. (8):

$$\lambda^{(i+1)} - \lambda^{(i)} = [\lambda_0^{(i+1)} - \lambda_0^{(i)}]a \quad (11)$$

i.e. the distance between wavelengths, for two arbitrary filters for any given angle θ, is proportional to distance between the same wavelengths for normal incidence.

In general, the distances between wavelengths are decreased with increasing values of θ. However, the filter wavelength-angle characteristics for two filters with different center wavelengths do not intersect with each other, as shown from the following proof. Consider two different filter wavelengths: $\lambda^{(1)}$ and $\lambda^{(2)}$; they may belong to the same filter or to two different filters. Assume their value for the same angle value, θ, thus, they have form:

$$\lambda^{(1)} = \lambda_0^{(1)} a \quad (12)(a)$$

$$\lambda^{(2)} = \lambda_0^{(2)} a \quad (12)(b)$$

when the a factor has the same value (because the incident angle is the same). These two wavelength characteristics: (11a) and (11b) can cross only when: $\lambda^{(1)} = \lambda^{(2)}$, but then, from Eq. (12), $\lambda_0^{(1)} = \lambda_0^{(2)}$; i.e., two different wavelength characteristics cannot intersect.

Figure 7:
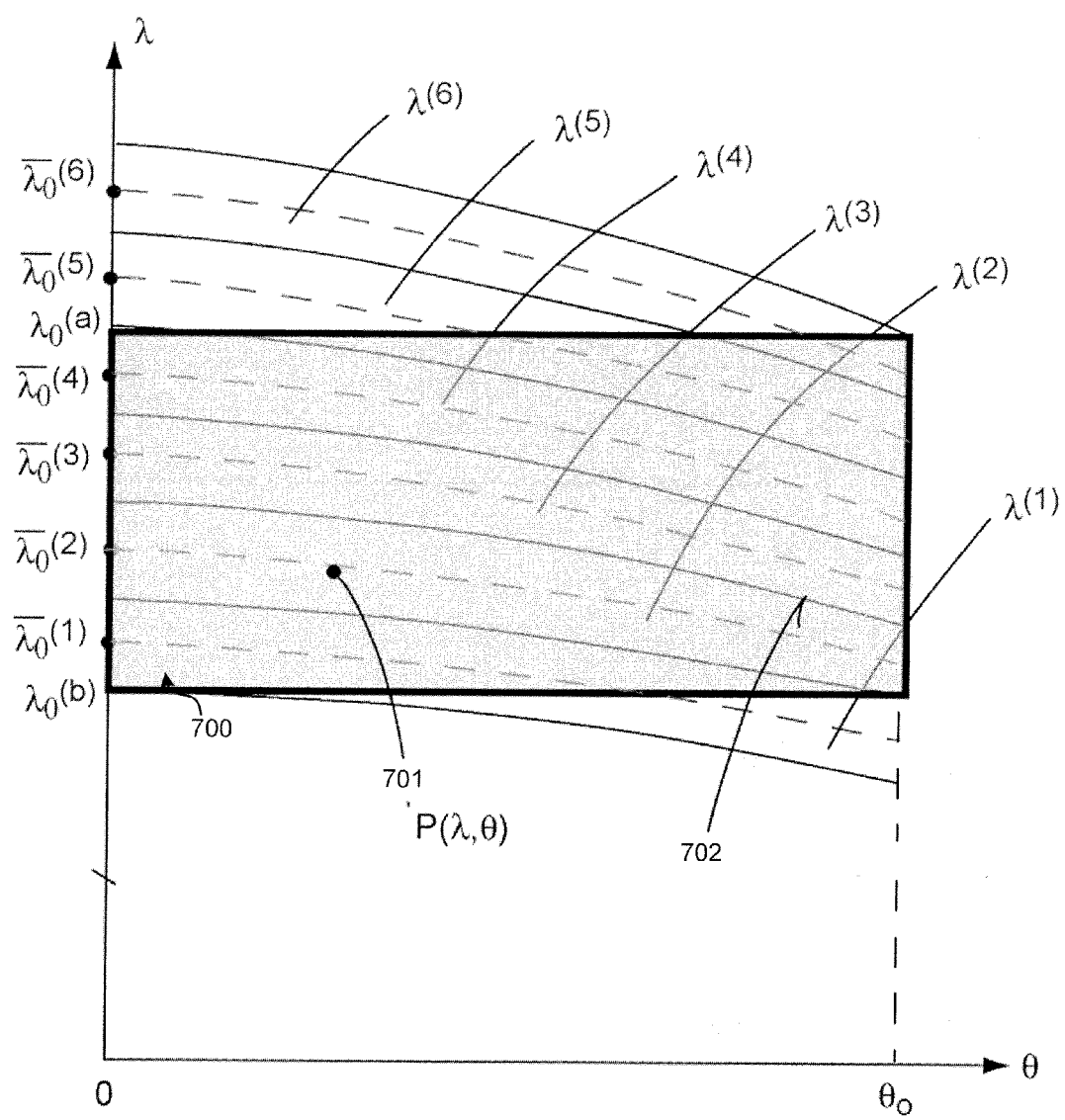

In some embodiments, the filters are selected to cover the spectral region (a band) between two predetermined wavelength values: $\lambda_0^{(a)}$ and $\lambda_0^{(b)}$, for a predetermined field of view of all θ-values between 0 to $\theta_o$. The graphical construction, illustrating the filter characteristics of an embodiment meeting these conditions, is shown in FIG. 7, where area 700 covers the region: $(\lambda_0^{(a)}, \lambda_0^{(b)})$ and $(0, \theta_o)$; i.e., the spectro-angular region 700 of coverage.

In an embodiment employing blue-shifting filters and binarization, any point within the spectro-angular region 700: $[(\lambda_0^{(a)}, \lambda_0^{(b)}); (0, \theta_o)]$, such as point P(λ,θ) 701 is exclusive (unique) for a specific spectral unit and a specific pixel within the spectral unit (spectral units are indexed by super-script: $^{(i)}$). In some embodiments, this requirement is relaxed at boundary regions 702 between the spectro-angular coverage of different filters. For example, the filters may be selected or the binarization process may be performed to allow a small region of overlap at regions 702. In some embodiments, this overlapping region is used in the case when some spectral signatures of items of interest are located at the boundary regions 702. In these embodiments, the overlap at regions 702 can be eliminated, a posteriori, by electronic processing after any spectral signatures are identified.

FIG. 8 illustrates a spectral unit implemented in accordance with an embodiment of the invention. The illustrated embodiment is similar to that of FIG. 4, a filter 800 is disposed on the surface of a plano-convex lens 801. The lens 802 has a radius of curvature 802, R. A light receiving surface 803, such as the curved surface of an image sensor or bundle of optical fibers, is disposed to coincide with the geometric loci of foci of plane waves transformed by the lens-filter combination 801-800. This light receiving surface 803 has a radius of curvature $p_2$ 805. The illustrated embodiment, utilizing a plano-convex lens, is suitable for situations where the paraxial approximation holds, i.e. for small incident angles. In such situations, other axial lenses may be employed as well. For larger incidence angles, some embodiments employ ball lens or gradient index (GRIN) lenses, such as Luneburg lenses.

For the monochromatic case (i.e., a single wavelength), the geometrical loci of foci from plane waves is a surface known as the Petzval surface. This is a well known geometrical optics construction based on the Seidel theory of geometrical aberrations. The Petzval surface of the lens 801 for monochromatic light is illustrated as surface 804 with a radius of curvature $\rho_1$ 806. In the illustrated embodiment, the filter 800 exhibits a blue-shifting effect, as discussed above. Accordingly, the monochromatic case does not hold, and the light receiving surface 803 differs from the corresponding Petzval surface 804. For example, in the plano-convex lens in the paraxial approximation, the lens is described by the following lens formula:

$$\frac{1}{f} = (n-1)\left(\frac{1}{R}\right) \quad (13)$$

where n is the index of refraction of the lens medium (typically, a kind of glass, or plastic), f is the focal length, and R is the lens curvature; 1/f is termed the focusing power of the lens. According to Eq. (1), the transmitted wavelength decreases with increasing incident angle θ. In the case of normal dispersion (which holds outside of absorptive resonances), the index of refraction of a solid medium, such as glass, or plastic, increases with increasing frequency, or, conversely, with decreasing wavelength.

Accordingly, the lens' 801 focusing power, 1/f, increases as the incident angle θ increases, according to Eq. (13). Thus, in turn, radius of curvature 805, $\rho_2$, for the light receiving surface is smaller than that (806 $\rho_1$) for the Petzval surface:

$$\rho_2 < \rho_1$$

The phenomenological relation between refractive index, n, for solid medium and wavelength, λ, is called Sellmeir's dispersion formula. The transformation leading to relation (14) is as follows:

$$\lambda \searrow \quad n \nearrow \quad \left(\frac{1}{f}\right) \nearrow \quad f \searrow \quad \Rightarrow \rho \searrow \quad (15)$$

FIG. 9 illustrates a mapping procedure for spectral data received from a plurality of spectral units implemented in accordance with an embodiment of the invention. As discussed above with respect to FIG. 2, within the approximation that the object of interest 202 is sufficiently far from the spectral units 200, the specific location of a particular spectral unit 200 within the spectral imaging system's 200 dimensions 206 can be ignored, assuming:

$$r >> d \quad (16)$$

where r is the distance 204 between the world point 202 of interest and the imaging system 200, while d 206 is the characteristic dimension size of the system 200. Under this approximation, any world point 202 of a given scene is defined only by its spherical coordinates (θ,φ) 203, 205. of its emitted plane wave, which is the same for all spectral units 201.

Referring back to FIG. 9, the spectral signature 900 of a specific substance of interest (e.g., some type of explosives' residuum or toxic gas) has two characteristic wavelength peaks 905 and 906 at $\lambda_1$ and $\lambda_2$. The illustrated embodiment has a predetermined spectro-angular coverage with a band spectral coverage in the range $(\lambda_0^{(a)}, \lambda_0^{(b)})$ that encompasses with peaks 905 and 906. For example, as discussed above with respect to FIG. 7, a plurality of spectral units, having spectral imaging coverage that varies with angle of incidence, may be used in the embodiment. For sake of simplicity, in FIG. 9, two spectral units with coverage 903 and 907 are illustrated in graph 901. Spectral unit 903 has a wavelength width of coverage 910 and spectral unit 907 has a wavelength width of coverage 909. The center of the coverage bands 903 and 907 varies with angle of incidence as shown. Accordingly, if the substance of interest is within the field of view of the embodiment, then it produces two distinctive signals 904 and 908 at a particular angle of incidence 902. These signals 904 and 908 will be detected by the two different spectral units, for example those indexed by i=4 and i=2, having coverage 903 and 907, respectively.

As illustrated in graphs 900 and 901, detection occurs for the spectral units that cover the peaks 905 and 906. In other words, when:

$$\lambda_1 \approx \overline{\lambda}^{(2)}, \lambda_2 \approx \overline{\lambda}^{(4)}. \tag{17}$$

In some embodiments, which spectral units detect the peaks is determined by the size of the spectral bands of the spectral units; here, $(\Delta\lambda)^{(2)}$ 909 and $(\Delta\lambda)^4$ 910, respectively (as used herein, the superscripts are indices of filter lens units, $\lambda_0$ refers to wavelength value of the filter at normal incidence, $\lambda$ refers to the wavelength at slanted incidence at a given angle, $\theta$, and $\overline{\lambda}$ refers to central wavelength value at the filter).

A further detection condition, additional to detection of signals at the relevant spectral peaks, is co-location of the peaks. As illustrated in FIG. 9, graph 901, this requires first that the detection of peaks 904 and 908 occurs at the same angle of incidence 902. Co-location further requires that the signals occur at the same azimuthal angle $\phi$. In other words, co-location of the spectral peaks requires that:

$$\theta^{(2)} = \theta^{(4)} = \theta_o \tag{18}(a)$$

$$\phi^{(2)} = \phi^{(4)} = \phi_o \tag{18}(b)$$

FIG. 10 illustrates a method of substance identification implemented in accordance with an embodiment of the invention. In step 150, the system obtains data regarding the spectral signatures of various items of interest. For example, the system may obtain a look-up table of different spectral signatures. In general, the spectral reflection functions of objects of typical interest, such as explosive, toxins, camouflaged items or life forms, depend highly on terrain and environment. Accordingly, the spectral reflection (or transmission, for example, to detect a cloud of gas), functions may be predetermined during application planning. In this analysis, look-up tables, can be generated with the relevant spectral information. For example, a particular embodiment might be configured for the detection of TNT residue. A look-up table could provide particular spectral peaks for TNT when disposed on various surfaces and under various terrain and environmental characteristics. This will result in a plurality of spectral references for TNT, that may be checked against received spectral information from the spectral imaging system.

In step 151, filter digitization data is obtained. As described above with respect to FIG. 6. Filter digitization, such as filter binarization based on clipping, allows the filtering characteristics of specific filters of the plurality of filters to be regularized or normalized. This results in a regular signal response across a bandwidth $\Delta\lambda$ for each binarized filter. With the binarized filter data, a region of spectro-angular region of coverage may be determined as discussed above with respect to FIG. 7. After this process, the spectral response of the spectral imaging system is uniform across the covered spectro-angular region of coverage. For example, referring to FIG. 7, the pass band $\Delta\lambda$ for the 4th filter (with center frequency $\overline{\lambda}_0^{(4)}$) at 0° partially overlaps the pass-band $\Delta\lambda$ for the 5th filter (with center frequency $\overline{\lambda}_0^{(5)}$) $\theta_0°$. After filter binarization, the transmissivity of the two filters at the two angles is equalized. Accordingly, a spectral peak within the overlapping region will have the same signal strength at 0° as $\theta_0°$, although the signals will arise from different spectral units. As further discussed above, in some embodiments, the binarization process is further configured such that the filters of varying spectral units have border regions that overlap slightly 702. In some embodiments, these overlapping points are used in image stitching and removed prior to spectral analysis. Accordingly, after step 151 each spectral signal point (wavelength and angle) is located at a single spectral unit.

In step 152, a spectro-angular map for the spectral imaging system is obtained. For each spectral unit, pixel locations are mapped to corresponding angular and spectral points, as discussed above with respect to FIG. 7. As discussed above, different spectral units have different normal incidence wavelength values, according to the following equation:

$$\lambda^{(i)} = \lambda_o^{(i)} \sqrt{1 - \frac{\sin^2\theta^{(i)}}{n^2}} \tag{19}$$

which is a generalization of Eq. (1) for a given filter lens unit, indexed by "i", here i=1, 2, ..., N, where N is total number of filter lens units. The filters may have, in general, different spectral widths, $\Delta\lambda^{(i)}$ which, in addition, change with angle, O. In some embodiments, the number, N, of different spectral units is selected according to the condition:

$$\lambda_o^{(b)} \leq \lambda \leq \lambda_o^{(a)} \tag{20}$$

where $\lambda_o^{(a)}, \lambda_o^{(b)}$ defines the spectral range of interest. In further embodiments, additional filters may be used to increase the spectral range of interest, or the spectral resolution of the system.

In step 153, system calibration may be performed. In various embodiments, the scene of interest searched by the spectral imager can be passively sensed due to albedo or actively illuminated. In both cases, systems calibration may involve recording the scene with a lens and pixel group unit that lacks a filter. Without a filter, the total incident illumination on the system may be measured by determining the incidence intensity, $I_0$, in the form $I_0(\theta, \phi)$, which does not depend on $\lambda$ because the incident intensity is averaged trough all wavelengths received. In particular embodiments, the intensity is measured using the same type of lens as employed in the spectral units, but lacking a corresponding filter. The intensity $I^{(i)}$, measured by a given spectral unit with index i, is $$I^{(i)}(\theta,\phi;\lambda) = I_o(\theta,\phi) I_N^{(i)}(\theta,\phi;\lambda) \tag{21}$$

where the normalized intensity, $I_N^{(i)}$, is obtained by extracting the universal to $$I_N^{(i)}(\theta, \phi; \lambda) = \frac{I^{(i)}(\theta, \phi; \lambda)}{I_o(\theta, \phi)}. \tag{22}$$

In step 153, the intensity values read at the various spectral units are normalized according to Eq. (22).

In step 154, measurements of spectral peaks and their locations are performed. After filter digitization in step 151, the spectral peaks are normalized across the plurality of spectral units. The spectro-angular map obtained in step 152 may then be used to determine the locations of the spectral peaks. By comparing the angular locations of the spectral peaks the conditions (17) and (18), which can be written in the following general form:

$$\lambda_i \approx \overline{\lambda}^{(i)}, \lambda_j \approx \overline{\lambda}^{(j)}, \text{etc.} \qquad (23)(a)$$

$$\theta^{(i)} = \theta^{(j)} = \theta^{(k)}, \text{etc.} \qquad (23)(b)$$

$$\phi^{(i)} = \phi^{(j)} = \phi^{(k)}, \text{etc.} \qquad (23)(c)$$

where $\lambda_i, \lambda_j, \ldots, \lambda_M$, determine spectral peaks characterizing the specific spectral signature, with M-total number of the peaks belonging to the same signature. These conditions define conditions that the identified peaks belong to the same substance. The sufficient conditions is that those peaks belong to the same spectral signature.

In step 155, the co-located spectral peaks are identified as particular substances. The fewer the number of spectral peaks in a substance's spectrum, the higher the risk of a false alarm. Accordingly, the number of spectral peaks used in the look-up tables may be determined according to desired false alarm probability, processing considerations, number of targets to be identified, resolution, and other such considerations. In some embodiments, the identified substances may be output as a list of substances and their angular locations identified within a given scene.

FIG. 11 illustrates a further embodiment of the invention. In this embodiment, a spectral imaging system comprises a plurality of spectral units 250. Each spectral unit 250 comprises a first lens 251 and a second lens 252. Disposed between the first lens 251 and second lens 252 is a filter 255. For example, the lenses may comprise hemi-spherical half-ball lens, and may be in a barrel configuration for mounting purposes. In other embodiments, other lenses, such as plano-convex, convex, Luneburg, GRIN or other lenses may be employed. In particular embodiments, the filter 255 is disposed at the pupil of the system, and may comprise a narrow-band interference filter, such as a Fabry-Perot interference planar filter that exhibits a blue-shift with increasing angle of incidence, as described above. In other embodiments, other filters, such as absorption filters may be employed.

Spectral unit 250 further comprises a bundle 254 of optical fibers 257. The optical fibers 257 are oriented along the axes of rays 258 to accept light impinging upon the unit 250 at varying angles of incidence. Further, in the illustrated embodiment, the fibers are further configured such that they form a light curved receiving surface 259. The curvature of the receiving surface 259 is configured to coincide with the focal locations 256 of rays 258 imaged by lenses 251 and 252. As discussed above, in embodiments where filter 255 exhibits blue-shifting with increasing angle of incidence, the profile of surface 259 has a radius of curvature that is smaller than the radius of curvature for the geometric loci of focal points of the lenses 251 and 252 without filter 255. In some embodiments, the bundle 254 may comprise a fiber optic taper. In other embodiments, the bundle 254 may comprise a portion of a fiber optic taper. The bundle 254 has a light outputting surface disposed on a plurality of pixel sensors 260. In some embodiments, the plurality of pixels 260 may make up image sensor 253, such as a CCD or CMOS image sensor. In other embodiments, the plurality of pixels 260 may comprise a portion of such an image sensor.

FIG. 12 illustrates another embodiment of the invention. In this embodiment, a spectral imaging system comprises a plurality of spectral units 270. A spectral unit 270 comprises a lens 271, a filter 272, a bundle 273 of optical fibers 276, and a plurality 274 of pixel sensors 277. In the illustrated embodiment, the lens 271 comprises a single ball lens in a barrel lens configuration. As discussed above, other lenses may be employed in other embodiments. The lens images rays 275 onto the curved light receiving surface 278 of the bundle 273 of optical fibers 276. In this embodiment, the filter 272 is curved to match the curved surface 278 and is disposed directly before the bundle 273 in the optical train of the unit 270. In this embodiment, the filter 272 may comprises an absorption filter, such as a holographic absorption filter. The fibers 276 of the bundle 273 are angled to be aligned with the axes of the imaged rays 275 that are receivable by the unit 270. In other embodiments, other filters may be employed. In the illustrated embodiment, the rays 275 do not pass through the filter 272 at varying angles of incidence. Rather, because the rays are almost point-like when filtered by the filter 272, and because the filter 272 is curved to match the light receiving surface 278, the rays 275 are substantially normal to the filter 272. Accordingly, the spectral unit 270 has a single central wavelength that does not vary with angle of incidence of received rays 275. In these embodiments, multispectral imaging capacity, rather than hyperspectral imaging capacity, may be achieved by providing filters 272 with different central wavelengths for different spectral units 270 of the multispectral imaging system. In the illustrated embodiment, the curved light receiving surface 278 is disposed to coincide with the Petzval's surface of the lens 271 because there is no blue-shifting of the filtered rays 275.

In some embodiments, a spectral imaging system may comprise a plurality of spectral units of one type, and a second plurality of spectral units of another type. For example, a particular spectral imaging system may comprise a plurality of spectral units 250, and second plurality of spectral units 270. For example, the system may have hyperspectral imaging capacity over a first predetermined band, such as near infrared and visible light, using a first plurality of units 250. The system may further achieve multispectral imagining capacity over a second predetermined band, such as mid and long wave infrared, using a second plurality of units 270.

FIG. 13 illustrates a further embodiment of the invention. In the illustrated embodiment, the spectral imaging syste 350 comprises a plurality of spectral units 351. In this embodiment, a spectral unit 351 comprises a telescope 353, a filter 353, a lens 354, a bundle of fiber optics 355, a plurality of pixel sensors 357, and a image processor 358. In some embodiments, the telescope 352 comprises a Galileo-type telescope, for example with about 5× zoom, and field of view between 60° and 90°. In this embodiment, filter 353 is disposed in the optical train after the telescope 352 and before the lens 354. The filter 353 may comprise an interference filter, and may exhibit a blue-shifting effect for hyperspectral imaging, as discussed above. In other embodiments, the filter may be disposed after lens 354 and before the light receiving surface 356 of the bundle 355, for example as discussed above with respect to FIG. 12. In this embodiment, lens 354 is disposed after the filter 353 and prior to the light receiving surface 356 of the bundle 355. In some embodiments, the lens 354 comprises a ball lens, in other embodiments, other lenses may be employed. The light receiving surface 356 is configured to coincide with the geometric foci of light rays emanating from the telescope 352 and transformed by the filter 353 and lens 354.

In the illustrated embodiment, the fiber optic bundle 355 constitutes an entire fiber optic taper. Each fiber optic bundle 355 is coupled to an image sensor 357. In some embodiments, the image sensors 357 may comprise visual to shortwave IR sensors, such as indium gallium arsenide or mercury cadmium telluride sensors. Each image sensor 357 is coupled to an image processor 358. In some embodiments, the image processors 358 is configured to perform various automatic transforms on the signal received from the sensor 357. For example, these processes might comprise filter digitization processes, spectro-angular mapping, or other processes as described herein.

As used herein, the term module might describe a given unit of functionality that can be performed in accordance with one or more embodiments of the present invention. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the invention are implemented in whole or in part using software, in one embodiment, these software elements can be implemented to operate with a computing or processing module capable of carrying out the functionality described with respect thereto. One such example computing module is shown in FIG. 14. Various embodiments are described in terms of this example—computing module 1000. After reading this description, it will become apparent to a person skilled in the relevant art how to implement the invention using other computing modules or architectures.

Referring now to FIG. 14, computing module 1000 may represent, for example, computing or processing capabilities found within desktop, laptop and notebook computers: handheld computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 1000 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 1000 might include, for example, one or more processors, controllers, control modules, or other processing devices, such as a processor 1004. Processor 1004 might be implemented using a general-purpose or special-purpose processing engine such as, for example, a microprocessor, controller, or other control logic. In the illustrated example, processor 1004 is connected to a bus 1002, although any communication medium can be used to facilitate interaction with other components of computing module 1000 or to communicate externally.

Computing module 1000 might also include one or more memory modules, simply referred to herein as main memory 1008. For example, preferably random access memory (RAM) or other dynamic memory, might be used for storing information and instructions to be executed by processor 1004. Main memory 1008 might also be used for storing temporary variables or other intermediate information during execution of instructions to be executed by processor 1004. Computing module 1000 might likewise include a read only memory ("ROM") or other static storage device coupled to bus 1002 for storing static information and instructions for processor 1004.

The computing module 1000 might also include one or more various forms of information storage mechanism 1010, which might include, for example, a media drive 1012 and a storage unit interface 1020. The media drive 1012 might include a drive or other mechanism to support fixed or removable storage media 1014. For example, a hard disk drive, a floppy disk drive, a magnetic tape drive, an optical disk drive, a CD or DVD drive (R or RW), or other removable or fixed media drive might be provided. Accordingly, storage media 1014 might include, for example, a hard disk, a floppy disk, magnetic tape, cartridge, optical disk, a CD or DVD, or other fixed or removable medium that is read by, written to or accessed by media drive 1012. As these examples illustrate, the storage media 1014 can include a computer usable storage medium having stored therein computer software or data.

In alternative embodiments, information storage mechanism 1010 might include other similar instrumentalities for allowing computer programs or other instructions or data to be loaded into computing module 1000. Such instrumentalities might include, for example, a fixed or removable storage unit 1022 and an interface 1020. Examples of such storage units 1022 and interfaces 1020 can include a program cartridge and cartridge interface, a removable memory (for example, a flash memory or other removable memory module) and memory slot, a PCMCIA slot and card, and other fixed or removable storage units 1022 and interfaces 1020 that allow software and data to be transferred from the storage unit 1022 to computing module 1000.

Computing module 1000 might also include a communications interface 1024. Communications interface 1024 might be used to allow software and data to be transferred between computing module 1000 and external devices. Examples of communications interface 1024 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1024 might typically be carried on signals, which can be electronic, electromagnetic (which includes optical) or other signals capable of being exchanged by a given communications interface 1024. These signals might be provided to communications interface 1024 via a channel 1028. This channel 1028 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 1008, storage unit 1020, media 1014, and channel 1028. These and other various forms of computer program edia or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 1000 to perform features or functions of the present invention as discussed herein.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A spectral imaging system, comprising:
    a plurality of spectral units arranged in an array, each spectral unit of the plurality of spectral units comprising:
    a microlens having an optical axis;
    a spectral filter having a center wavelength and aligned with the optical axis, the spectral filter comprising an interference filter and wherein the center wavelength of each spectral filter varies according to an incident angle light impinging upon the spectral filter;
    a fiber optic bundle, the fiber optic bundle having a curved light receiving surface and a planar light output surface, wherein the curved light receiving surface is aligned with the optical axis and coincides with a surface of geometric foci of planes waves transformed by the spectral unit's spectral filter and microlens; and
    a plurality of pixel sensors configured to receive light from the planar light output surface of the filter optic taper portion.

2. The spectral imaging system of claim 1, wherein each spectral unit at the plurality of spectral unit further comprises a channel of a microchannel array.

3. The spectral imaging system of claim 1, wherein:
    the microlenses of the plurality of spectral units form a microlens array;
    the fiber optic bundles of the plurality of spectral units form a fiber optic taper; and
    the pluralities of pixel sensors of the plurality of spectral units form an image sensor.

4. The spectral imaging system of claim 1, wherein, for each spectral unit, the curved light receiving surface of the spectral unit's fiber optic bundle has a radius of curvature that is smaller than the radius of curvature of a Petzval surface of an optical system comprising the spectral unit's microlens without the spectral filter.

5. The spectral imaging system of claim 1, wherein, for each spectral unit, the spectral unit's spectral filter is disposed before the spectral microlens such that light impinging on the spectral unit is filtered by the spectral unit's spectral filter before being refracted by the spectral unit's microlens.

6. The spectral imaging system of claim 1, wherein each spectral unit further comprises a second microlens and, for each spectral unit, the spectral filter is disposed between the first microlens and the second microlens.

7. The spectral imaging system of claim 1, wherein the plurality of spectral filters have varying center frequencies configured to provide a predetermined spectral coverage within a predetermined field of view.

8. The spectral imaging system of claim 7, further comprising a digital system coupled to the pluralities of pixel sensors of the plurality of spectral units, the digital system comprising:
a spectro-angular map that maps coordinates comprising spectral filter center frequencies and angular locations to coordinates of pixels of the pluralities of pixel sensors of the plurality of spectral units.

9. The spectral imaging system of claim 8, wherein the digital system further composes a table of substance and their corresponding spectral signatures.

10. The spectral imaging system of claim 9, wherein the digital system further comprises hardware or software logic configured to digitize values received from the pluralities of pixel sensors of the plurality spectral units.

11. The spectral imaging system of claim 10, wherein the hardware or software logic is further configured uses the digitized values to provide a measurement of a spectra/peak and an angular location for the spectral peak.

12. The spectral imaging system of claim 11, wherein the hardware or software logic is configured to use the measurement of the spectral peak and the table of substances and their corresponding spectral signatures to detect a substance and angular location for the detected substance.

13. A method of spectral imaging, comprising:
receiving light using a plurality of spectral units arranged in an array, each spectral unit of the plurality of spectral units comprising:
a microlens having an optical axis;
a spectral filter having a center wavelength and aligned with the optical axis, the spectral filter comprising an interference filter and wherein the center wavelength of each spectral filter varies according to an incident angle of light impinging upon the spectral filter;
a fiber optic bundle, the fiber optic bundle having a curved light receiving surface and as planar light output surface, wherein the curved light receiving surface is aligned with the optical axis and coincides with a surface of geometric foci of planes waves transformed by the spectral unit's spectral filter and microlens; and
a plurality of pixel sensors configured to receive light from the planar light output surface of the fiber optic taper portion.

14. The method of claim 13, wherein, for each spectral unit, the curved light receiving surface of the spectral unit's fiber optic bundle has a radius of curvature that is smaller than the radius of curvature of a Petzval surface of an optical system comprising the spectral unit's microlens without the spectral filter.

15. The method of claim 13, wherein, for each spectral unit, the spectral unit's spectral filter is disposed before the spectral unit's microlens such that light impinging on the spectral unit is filtered by the spectral unit's spectral filter before being refracted by the spectral units microlens.

16. The method of claim 13, wherein each spectral unit further comprises at second microlens and, for each spectral unit, the spectral filter is disposed between the first microlens and the second microlens.

17. The method of claim 13, wherein the plurality of spectral filters have varying center frequencies configured to provide a predetermined spectral coverage within a predetermined field of view.

18. The method of claim 17, further comprising transmitting signals from the pluralities of pixel sensors of the plurality of spectral units to a digital system coupled to the pluralities of pixel sensors of the plurality of spectral units, the digital system comprising:
spectro-angular map that maps coordinates comprising spectral filter center frequencies and angular locations to coordinates of pixels of the pluralities of pixel sensors of the plurality of spectral units.

19. The method of claim 18, wherein the digital system further comprises a table of substances and their corresponding spectral signatures.

20. The method of claim 19, wherein the digital system further comprises hardware or software logic configured to digitize values received from the pluralities of pixel sensors of the plurality of spectral units.

21. The method of claim 20, wherein the hardware or software logic is further configured to use the digitized values to provide a measurement of a spectral peak and an angular location for the spectral peak.

22. The method of claim 21, wherein the hardware or software logic is configured to use the measurement of the spectral peak and the table of substances and their corresponding spectral signatures to detect a substance and angular location for the detected substance.

23. A spectral imaging system, comprising:
a plurality of spectral units arranged in an array, each spectral unit of the plurality of spectral units comprising:
a microlens having an optical axis;
a spectral filter having a center wavelength and aligned with the optical axis, the spectral filter comprising an absorption-type filter and being curved;
a fiber optic bundle, the fiber optic bundle having a curved light receiving surface and a planar light output surface, wherein the curved light receiving surface is aligned with the optical axis, wherein the spectral filter is disposed adjacent to the curved, light receiving surface; and
plurality of pixel sensors configured to receive light born the planar light output surface of the fiber optic taper portion.

24. The spectral imaging system of claim 23, wherein each spectral unit of the plurality of spectral unit further comprises a channel of a microchannel array.

25. The spectral imaging system of claim 23, wherein:
the microlenses of the plurality of spectral units form a microlens arrays,
the fiber optic bundles of the plurality of spectral units form a fiber optic taper; and
the pluralities of pixel sensors of the plurality of spectral units form an image sensor.

26. The spectral imaging system of claim 23, wherein each spectral filter comprises a holographic spectral filter.

27. The spectral imaging system of claim 23, wherein, for each spectral unit, the curved light receiving portion of the spectral units fiber optic bundle coincides with a Petzval surface of the spectral unit's microlens.

28. The spectral imaging system of claim 23, wherein the plurality or spectral filters have varying center frequencies configured to provide a predetermined spectral coverage within a predetermined field of view.

29. The spectral imaging system of claim 28, further comprising a digital system coupled to the pluralities of pixel sensors of the plurality of spectral units, the digital system comprising:
a spectro-angular map that maps coordinates comprising spectral filter center frequencies and angular locations to coordinates of pixels of the pluralities of pixel sensors of the plurality of spectral units.

30. The spectral imaging system of claim 29, wherein the digital system further comprises a table of substances and their corresponding spectral signatures.

31. The spectral imaging system of claim 30, wherein the digital system further comprises hardware or software logic configured to digitize values received from the pluralities of pixel sensors of the plurality of spectral units.

32. The spectral imaging system of claim 31, wherein the hardware or software logic is further configured uses the digitized values to provide a measurement or a spectral peak and an angular location for the spectral peak.

33. The spectral imaging system of claim 32, wherein the hardware or software logic is configured to use the measurement of the spectral peak and the table of substances and their corresponding spectral signatures to detect a substance and angular location for the detected substance.

34. A method of spectral imaging, comprising:
receiving light using plurality of spectral units arranged in an array, each spectral unit of the plurality of spectral units comprising:
microlens having an optical axis;
a spectral filter having a center wavelength and aligned with the optical axis, the spectral filter comprising an absorption-type fiber and being curved;
a fiber optic bundle, the fiber optic bundle having a curved light receiving surface and to planar light output surface, wherein the curved light receiving surface is aligned with the optical axis, wherein the spectral filter is disposed adjacent to the curved light receiving surface; and
a plurality of pixel sensors configured to receive light from the planar light output surface of the fiber optic taper portion.

35. The method of claim 34, wherein each spectral filter comprises a holographic spectral filter.

36. The method of claim 34, wherein, for each spectral unit, the curved light receiving portion of the spectral units fiber optic bundle coincides with a Petzval surface of the spectral unit's microlens.

37. The method of claim 34, wherein the plurality of spectral filters have varying center frequencies configured to provide a predetermined spectral coverage within a predetermined field of view.

38. The method of claim 37, further comprising transmitting signals from the pluralities of pixel sensors of the plurality of spectral units to a digital system coupled to the pluralities of pixel sensors of the plurality of spectral wilts, the digital system comprising:
a spectro-angular map that maps coordinates comprising spectral filler center frequencies and angular locations to coordinates of pixels of the pluralities of pixel sensors of the plurality of spectral units.

39. The method of claim 38, wherein the digital system further comprises a table of substances and their corresponding spectral signatures.

40. The method of claim 39, wherein the digital system further comprises hardware or software logic configured to digitize values received from the pluralities of pixel sensors of the plurality of spectral units.

41. The method of claim 40, wherein the hardware or software logic is further configured uses the digitized values to provide a measurement of a spectral peak and an angular location for the spectral peak.

42. The method of claim 41, wherein the hardware or software logic is configured to use the measurement of the spectral peak and the table of substances and their corresponding spectral signatures to detect a substance and angular location for the detected substance.

* * * * *

UNITED STATES PATENT AND TRADEMARK OFFICE
CERTIFICATE OF CORRECTION

PATENT NO.         : 8,665,440 B1
APPLICATION NO.    : 13/025096
DATED              : March 4, 2014
INVENTOR(S)        : Iouri Kompaniets et al.

It is certified that error appears in the above-identified patent and that said Letters Patent is hereby corrected as shown below:

In the Claims

Claim 9, Column 17, line 11, "digital system further composes" should read --digital system further comprises--

Signed and Sealed this
Tenth Day of June, 2014

Michelle K. Lee
*Deputy Director of the United States Patent and Trademark Office*